United States Patent [19]

Brana et al.

[11] 4,288,597
[45] Sep. 8, 1981

[54] 1,2-DIACYLAMINO-1,2-DI(4-PYRIDYL)ETHANES AND PROCESS FOR PRODUCING THEREOF

[75] Inventors: Miguel F. Brana; Maria L. López Rodriguez; José M. Castellano Berlanga; José L. Soto Cámara; Cristóbal Martinez Roldan, all of Madrid, Spain

[73] Assignee: Laboratorios Made, S.A., Madrid, Spain

[21] Appl. No.: 128,427

[22] Filed: Mar. 10, 1980

[30] Foreign Application Priority Data

Apr. 26, 1979 [ES] Spain .................................. 479.959

[51] Int. Cl.³ .......................................... C07D 401/06
[52] U.S. Cl. .................................................. 546/265
[58] Field of Search ........................................ 546/265

[56] References Cited

U.S. PATENT DOCUMENTS 2,493,068  1/1950  Hunt et al. ........................... 546/265

Primary Examiner—John M. Ford
Attorney, Agent, or Firm—Ladas & Parry

[57] ABSTRACT

1,2-diacylamino-1,2-di(4-pyridil)ethanes of general formula:

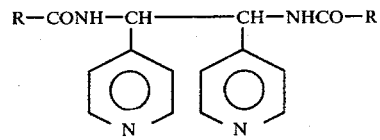

where R is a saturated or unsaturated alkyl group, a homocyclic or heterocyclic aromatic ring, with or without substituents, or a saturated or unsaturated cycloalkyl. Said compounds are useful as analgesic. A process for preparing such products is also described.

22 Claims, No Drawings

1,2-DIACYLAMINO-1,2-DI(4-PYRIDYL)ETHANES AND PROCESS FOR PRODUCING THEREOF

This invention relates to the industrial production of 1,2-diacylamino-1,2-di(4-pyridyl)ethanes of general formula

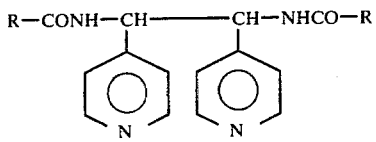

where R is a saturated or unsaturated alkyl group, a homocyclic or heterocyclic aromatic ring, with or without substituents, or a saturated or unsaturated cycloalkyl based on the reaction of an N-(4-picolyl)-amide or preferably its N-oxide of formula:

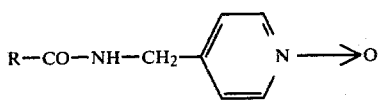

where R has the aforementioned meaning by treatment with acid halides or anhydrides, of which acetic anhydride is preferred, at reflux temperature and in general at temperatures above 110° C., in the presence of a solvent, although the actual derivative of the acid will preferably be used as such, between one and twenty-four hours, the product precipitating within the reaction, being filtered and purified by crystallization within a suitable solvent in the usual manner.

These compounds are interesting because of the pharmacological properties which will be indicated later on in this specification.

A series of examples which do not limit the scope of this invention are expounded below.

EXAMPLE 1

(R is $CH_3$—)

5 g. of N-(4-picolyl)-acetamide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The acetic anhydride is evaporated under vacuum and the residue is treated with 30 ml. of ethyl acetate. The solid obtained is recrystallized from N-N-dimethylformamide. M.P. >250° C., Yield 1 g. (20%).

Analysis: Calculated for $C_{16}H_{18}O_2N_4$; C: 64.41; H: 6.08; N: 18.78. Found: C: 64.17; H: 6.13; N: 18.63.

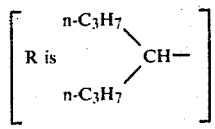

EXAMPLE 2

5 g. of N-(4-picolyl)-2-n-propyl valeramide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from ethanol. M.P. >250° C. Yield 2 g. (43%).

Analysis: Calculated for $C_{28}H_{42}O_2N_4$; C: 72.06; H: 9.07; N: 12.00. Found: C: 72.31; H: 8.94; N: 11.68.

EXAMPLE 3

(R is $C_6H_5$—)

5 g. of N-(4-picolyl)-benzamide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The acetic anhydride is evaporated under vacuum and the residue is treated with 30 ml. of ethyl acetate. The solid obtained is recrystallized from N-N-dimethylformamide. M.P. >250° C. Yield 1.2 (25%).

Analysis: Calculated for $C_{26}H_{22}O_2N_4$; C: 73.91; H: 5.24; N: 13.26. Found: C: 74.01; H: 5.15; N: 12.97.

EXAMPLE 4

(R is 4—$CH_3$—$C_6H_4$—)

5 g. of N-(4-picolyl)-4-methylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 2 g. (44%).

Analysis: Calculated for $C_{28}H_{26}O_2N_4$; C: 74.64; H: 5.81; N: 12.43. Found: C: 74.39; H: 6.08; N: 12.60.

EXAMPLE 5

(R is 3—$CH_3$—$C_6H_4$—)

5 g. of N-(4-picolyl)-3-methylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide-water. M.P. >250° C. Yield 1.9 (42%).

Analysis: Calculated for $C_{18}H_{26}O_2N_4$; C: 74.64; H: 5.81; N: 12.43. Found: C: 74.87; H: 5.63; N: 12.60.

EXAMPLE 6

(R is 2—$CH_3$—$C_6H_4$—)

5 g. of N-(4-picolyl)-2-methylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1.8 (39%).

Analysis: Calculated for $C_{28}H_{26}O_2N_4$; C: 74.64; H: 5.81; N: 12.43. Found: C: 74.80; H: 5.75; N: 12.62.

EXAMPLE 7

(R is 3,5—$(CH_3)_2$—$C_6H_3$—)

5 g. of N-(4-picolyl)-3,5-dimethylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 2 g. (43%).

Analysis: Calculated for $C_{30}H_{30}O_2N_4$; C: 75.28; H: 6.31; N: 11.70. Found: C: 75.16; H: 6.41; N: 11.90.

EXAMPLE 8

(R is 4—Cl—$C_6H_4$—)

5 g. of N-(4-picolyl)-4-chlorobenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1.8 (39%).

Analysis: Calculated for $C_{26}H_{20}O_2N_4Cl_2$; C: 62.78; H: 4.15; N: 11.64; Cl: 14.76. Found: C: 62.93; H: 3.88; N: 11.52; Cl: 14.85.

EXAMPLE 9

(R is 3—Cl—$C_6H_4$—)

5 g. of N-(4-picolyl)-3-chlorobenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1.7 (37%).

Analysis: Calculated for $C_{26}H_{20}O_2N_4Cl_2$; C: 62.78; H: 4.15; N: 11.64; Cl: 14.76. Found: C: 62.84; H: 3.95; N: 11.49; Cl: 14.88.

EXAMPLE 10

(R is 2—Cl—$C_6H_4$—)

5 g. of N-(4-picolyl)-2-chlorobenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1.8 g. (39%).

Analysis: Calculated for $C_{26}H_{20}O_2N_4Cl_2$; C: 62.78; H: 4.15; N: 11.64; Cl: 14.76. Found: C: 63.05; H: 3.84; N: 11.48; Cl: 14.84.

EXAMPLE 11

(R is 3,5—$Cl_2$—$C_6H_3$—)

5 g. of N-(4-picolyl)-3,5-dichlorobenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1.8 (38%).

Analysis: Calculated for $C_{26}H_{18}O_2N_4Cl_4$; C: 55.71; H: 3.21; N: 10.00; Cl: 25.35. Found: C: 55.51; H: 3.50; N: 10.20; Cl: 25.09.

EXAMPLE 12

(R is 4—F—$C_6H_4$—)

5 g. of N-(4-picolyl)-4-fluorbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide-water. M.P. >250° C. Yield 1.5 g. (33%).

Analysis: Calculated for $C_{26}H_{20}O_2N_4F_2$; C: 68.12; H: 4.36; N: 12.22. Found: C: 67.94; H: 4.14; N: 12.44.

EXAMPLE 13

(R is 4—$F_3C$—$C_6H_4$—)

5 g. of N-(4-picolyl)-4-trifluormethylbenzamide N-oxide are plaed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid obtained is filtered, washed with ethyl acetate and recrystallized from N-N-dimethylformamide. M.P. >250° C. Yield 1.8 g. (38%).

Analysis: Calculated for $C_{28}H_{20}O_2N_4F_6$; C: 60.21; H: 3.58; N: 10.08. Found: C: 60.03; H: 3.50; N: 9.95.

EXAMPLE 14

(R is 4—$CH_3O$—$C_6H_4$—)

5 g. of N-(4-picolyl)-4-methoxybenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide-water. M.P. >250° C. Yield 2 g. (43.5%).

Analysis: Calculated for $C_{28}H_{26}O_2N_4$; C: 69.69; H: 5.43; N: 11.61. Found: C: 69.31; H: 5.14; N: 11.41.

EXAMPLE 15

(R is 4—$CH_3$—$SO_2$—$C_6H_4$—)

5 g. of N-(4-picolyl)-4-mesylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N,N-dimethylformamide-methanol. M.P. >250° C. Yield 3 g. (64%).

Analysis: Calculated for $C_{28}H_{26}O_6N_4S_2$; C: 58.12; H: 4.53; N: 9.68; S: 11.09. Found: C: 57.93; H: 4.26; N: 9.39; S: 11.09.

EXAMPLE 16

(R is 4—$NO_2$—$C_6H_4$—)

5 g. of N-(4-picolyl)-4-nitrobenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N,N-dimethylformamide-water. M.P. >250° C. Yield 2.5 g. (54%).

Analysis: Calculated for $C_{26}H_{20}O_6N_6$; C: 60.93; H: 3.93; N: 16.40. Found: C: 60.80; H: 4.04; N: 16.11.

EXAMPLE 17

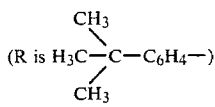

(R is $H_3C-\underset{\underset{CH_3}{|}}{\overset{\overset{CH_3}{|}}{C}}-C_6H_4-$)

5 g. of N-(4-picolyl)-4-tertbutylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 3.3 g. (70%).

Analysis: Calculated for $C_{34}H_{38}O_2N_4$; C: 76.37; H: 7.16; N: 10.47. Found: C: 76.30; H: 6.89; N: 10.53.

EXAMPLE 18

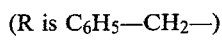

(R is $C_6H_5-CH_2-$)

5 g. of N-(4-picolyl)-phenylacetamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1 g. (22%).

Analysis: Calculated for $C_{28}H_{26}O_2N_4$; C: 74.64; H: 5.81; N: 12.43. Found: C: 74.59; H: 5.86; N: 12.37.

EXAMPLE 19

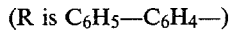

(R is $C_6H_5-C_6H_4-$)

5 g. of N-(4-picolyl)-4-phenylbenzamide N-oxide are placed in a two-neck flask with a capacity of 100 ml., provided with reflux coolant and a drop funnel, and 35 ml. of acetic anhydride are slowly added. Once the addition is completed, the mixture is heated to reflux for 1.5 hours. The solid formed is filtered, washed with ethyl acetate and recrystallized from N-N-dimethylformamide. M.P. >250° C. Yield 1.9 g. (40%).

Analysis: Calculated for $C_{38}H_{30}O_2N_4$; C: 79.41; H: 5.26; N: 9.75. Found: C: 79.20; H: 5.44; N: 10.04.

PHARMACOLOGICAL PROPERTIES OF THE PRODUCTS OF THE INVENTION

There is a series of 19 products, with analgesic activity, the effects whereof were tested using dextropropoxyphene as a reference drug.

The object of the studies carried out on all the products was to calculate the acute toxicity, expressed in the form of lethal dose 50, and to evaluate the analgesic effect by administering the drugs orally and intraperitoneally.

A—ACUTE TOXICITY

Tests were carried out on I.C.R. Swiss albino mice of both sexes weighing between 20 and 35 grams. The products were administered intraperitoneally, recording the number of dead animals three days after administration of the drugs. The statistical method used for the calculation of lethal dose 50 was the Litchfield-Wilcoxon method. The results are given in Table A.

TABLE A

| Treatments Products: | ACUTE TOXICITY Lethal Dose 50 (mg/kg) |
|---|---|
| Dextropropoxyphene | 140 |
| Product of Example 1 | 1124.9 |
| Product of Example 2 | >1600 |
| Product of Example 3 | >1300 |
| Product of Example 4 | >1665 |
| Product of Example 5 | >1400 |
| Product of Example 6 | >1600 |
| Product of Example 7 | >1600 |
| Product of Example 8 | >1600 |
| Product of Example 9 | >1300 |
| Product of Example 10 | 1064.3 |
| Product of Example 11 | >1200 |
| Product of Example 12 | 1107.7 |
| Product of Example 13 | >1200 |
| Product of Example 14 | >1600 |
| Product of Example 15 | >2000 |
| Product of Example 16 | >1600 |
| Product of Example 17 | >1600 |
| Product of Example 18 | 1540 |
| Product of Example 19 | >1600 |

It can be observed that all the tested products have lower acute toxicity than dextropropoxyphene.

B—ANALGESIC EFFECT

1. ACTIVITY BY INTRAPERITONEAL ROUTE

The analgesic effect was evaluated according to the technique of Siegmund et al. (Proc. Soc. Exp. Biol. Med. 95, 729, 1957) modified by Koster et al. (Fed. Proc. 18, 412, 1957), a chemical analgesia test which uses 1% acetic acid as an irritant. The drugs under study were administered at the dose of 1 mg/kg and the reference drug at 25 mg/kg. The evaluation was made 30 minutes after the administrations. The results are given in Table B-1, expressing the results in the form of relative potency (F), giving dextropropoxyphene value 1.

$$F = \frac{\text{Activity of drug under study}}{\text{Activity of dextropropoxyphene}}$$

TABLE B - 1

| Treatments Products: | ANALGESIC EFFECT BY INTRAPERITONEAL ROUTE F |
|---|---|
| Dextropropoxyphene | 1 |
| Product of Example 1 | 1.01 |
| Product of Example 2 | 1.43 |
| Product of Example 3 | 1.21 |
| Product of Example 4 | 1.04 |
| Product of Example 5 | 1.85 |
| Product of Example 6 | 1.09 |
| Product of Example 7 | 1.53 |
| Product of Example 8 | 1.58 |
| Product of Example 9 | 1.08 |
| Product of Example 10 | 1.37 |
| Product of Example 11 | 0.84 |
| Product of Example 12 | 1.17 |
| Product of Example 13 | 1.38 |
| Product of Example 14 | 1.09 |
| Product of Example 15 | 1.43 |
| Product of Example 16 | 1.38 |
| Product of Example 17 | 1.11 |
| Product of Example 18 | 0.96 |
| Product of Example 19 | 1.08 |

2. ACTIVITY BY ORAL ROUTE

The foregoing procedure was used, with the difference that the dose of the products under study was 5 mg/kg. The results are given in table B-2.

TABLE B - 2

| ANALGESIC EFFECT BY ORAL ROUTE | |
|---|---|
| Treatments Products: | F |
| Dextropropoxyphene | 1 |
| Product of Example 1 | 0.85 |
| Product of Example 2 | 0.95 |
| Product of Example 3 | 1.35 |
| Product of Example 4 | 1.11 |
| Product of Example 5 | 1.64 |
| Product of Example 6 | 1.67 |
| Product of Example 7 | 1.17 |
| Product of Example 8 | 1.29 |
| Product of Example 9 | 1.05 |
| Product of Example 10 | 1.34 |
| Product of Example 11 | 1.22 |
| Product of Example 12 | 0.81 |
| Product of Example 13 | 1.19 |
| Product of Example 14 | 1.23 |
| Product of Example 15 | 1.05 |
| Product of Example 16 | 1.25 |
| Product of Example 17 | 1.17 |
| Product of Example 18 | 2.13 |
| Product of Example 19 | 1.13 |

C—INTESTINAL PASSAGE

The modification of intestinal passage was evaluated with the activated carbon technique.

The drugs under study were administered at the dose of 36 mg/kg, the same as the reference drug (dextropropoxyphene). Thirty minutes after intraperitoneal injection of the drugs, the activated carbon is orally administered in suspension in gum arabic and allowed to act for 10 minutes, following which the animals are sacrificed and the length of the intestinal fragment travelled (traversed) by the carbon suspension is measured. The results are given in table C-1, in the form of relative potency (F, dextropropoxyphene being attributed value 1).

$$F = \frac{\text{Problem drug activity}}{\text{Dextropropoxyphene activity}}$$

TABLE C - 1

| INTESTINAL (PASSAGE (INTRAPERITONEAL) ROUTE) | |
|---|---|
| Treatments Products: | F |
| Dextropropoxyphene | 1 |
| Product of Example 1 | — |
| Product of Example 2 | 1.25 |
| Product of Example 3 | 0.67 |
| Product of Example 4 | 1.05 |
| Product of Example 5 | 0.94 |
| Product of Example 6 | 1.09 |
| Product of Example 7 | 0.62 |
| Product of Example 8 | 0.64 |
| Product of Example 9 | 1.08 |
| Product of Example 10 | 0.64 |
| Product of Example 11 | 0.74 |
| Product of Example 12 | 0.95 |
| Product of Example 13 | 0.42 |
| Product of Example 14 | 0.85 |
| Product of Example 15 | 0.83 |
| Product of Example 16 | 0.77 |
| Product of Example 17 | 0.74 |
| Product of Example 18 | 1.15 |
| Product of Example 19 | 0.69 |

We claim:
1. A compound of the formula

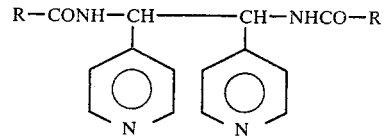

where R is an alkyl group of 1 to 7 carbon atoms; a phenyl group which may be substituted with an alkyl group of 1 to 4 carbon atoms, halogen, trifluromethyl, methoxy, methylsulfonyl or nitro; benzyl or diphenyl.

2. A process for the production of a 1,2-diacylamino-1,2-di(4-pyridyl)ethane of formula

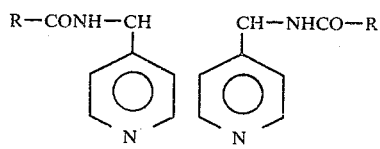

where R is an alkyl group of 1 to 7 carbon atoms; a phenyl group which may be substituted with an alkyl group of 1 to 4 carbon atoms, halogen, trifluromethyl, methoxy, methylsulfonyl or nitro; benzyl or diphenyl, which comprises reacting an N-(4-picolyl) amide or preferably its N-oxide of the formula

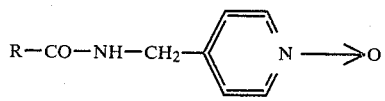

where R has the aforementioned meaning, with acid halides or acid anhydrides at temperatures above 110° C., with or without solvent, between 1 and 24 hours, the product precipitating within reaction and them being filtered and purified by crystallization in the usual manner.

3. A process according to claim 2 characterized in that R is methyl.

4. A process according to claim 2, characterized in that R is di-n- propylmethyl.

5. A process according to claim 2, characterized in that R is phenyl.

6. A process according to claim 2, characterized in that R is p-tolyl.

7. A process according to claim 2, characterized in that R is m-tolyl.

8. A process according to claim 2, characterized in that R is o-tolyl.

9. A process according to claim 2, characterized in that R is 3,5-dimethyl-phenyl.

10. A process according to claim 2, characterized in that R is p-chlorophenyl.

11. A process according to claim 2, characterized in that R is m-chlorophenyl.

12. A process according to claim 2, characterized in that R is o-chlorophenyl.

13. A process according to claim 2, characterized in that R is 3,5-dichlorophenyl.

14. A process according to claim 2, characterized that R is p-fluorophenyl.

15. A process according to claim 2, characterized in that R is p-trifluoro-methyl-phenyl.

16. A process according to claim 2, characterized in that R is p-anisyl.

17. A process according to claim 2, characterized in that R is p-mesyl-phenyl.

18. A process according to claim 2, characterized in that R is p-nitro-phenyl.

19. A process according to claim 2, characterized in that R is p-tertbutyl-phenyl.

20. A process according to claim 2, characterized in that R is benzyl.

21. A process according to claim 2, characterized in that R is p-biphenyl.

22. A process according to claim 2, characterized in that the anhydride used is acetic anhydride.

* * * * *